United States Patent [19] [11] 4,191,225

Ogle [45] Mar. 4, 1980

[54] PHARMACEUTICAL COCKTAIL PACKAGE

[75] Inventor: Robert W. Ogle, Newport Beach, Calif.

[73] Assignee: IMS Limited, South El Monte, Calif.

[21] Appl. No.: 866,380

[22] Filed: Jan. 3, 1978

Related U.S. Application Data

[63] Continuation of Ser. No. 734,254, Oct. 20, 1976, abandoned.

[51] Int. Cl.[2] .......... B65B 3/04; A61M 5/00

[52] U.S. Cl. .......... 141/329; 128/220; 128/272.3

[58] Field of Search .......... 128/2 F, DIG. 5, 214.2, 128/272.3, 272.1, 220, 218 M; 141/329

[56] References Cited

U.S. PATENT DOCUMENTS

| | | | |
|---|---|---|---|
| 2,847,995 | 8/1958 | Adams | 128/DIG. 5 |
| 3,734,080 | 5/1973 | Petterson et al. | 128/DIG. 5 |
| 3,877,465 | 4/1975 | Miyake | 128/DIG. 5 X |
| 3,972,330 | 8/1976 | Cloyd | 128/220 |
| 3,987,791 | 10/1976 | Chittenden et al. | 141/329 |
| 3,999,543 | 12/1976 | Lacey | 141/329 X |

*Primary Examiner*—Frederick R. Schmidt

*Attorney, Agent, or Firm*—Wills, Green & Mueth

[57] ABSTRACT

An alimentation kit comprising a plurality of cylindrical rigid vials, each containing a liquid concentrate of an alimentary component and a resilient slidable sealing piston stopper within the vial. The kit also includes a transfer device for the sequential addition of the liquid contents of each of said vials to a conventional container of intravenous solution. The transfer device has a cannula which is provided with a longitudinally extending rigid support, in proximity to one end of the rigid support a laterally extending flange, the laterally extending flange being adapted to act as a stop to limit the extent of advancement of the cannula. The other end portion of the cannula extends beyond the other end of said rigid support and terminates in a sharpened outer end. A thin resilient tube is provided over the sharpened outer end. The resilient tube is longitudinally compressible over and pierced by the sharpened outer end when the piston stopper of one of the vials is forced over the sharpened outer end whereby the contents of the vial can be transferred to the intravenous solution container through the cannula. The resilient tube is self-recoverable over the sharpened end when the piston stopper is withdrawn.

1 Claim, 10 Drawing Figures

PHARMACEUTICAL COCKTAIL PACKAGE

This is a continuation, of application Ser. No. 734,254, filed Oct. 20, 1976 now abandoned.

BACKGROUND OF THE INVENTION

Hyper-alimentation is becoming more common as a form of care for the seriously ill. Typically, a number of different nutrients, vitamins and electrolytes are administered intravenously to the patient. In general, these different ingredients are supplied or formulated in the form of a concentrate which is diluted with an ordinary intravenous solution at the time of administration. In many cases, the nutrient, vitamin and electrolyte concentrates are added to the intravenous solution in fixed ratios or percentages. However, many of these conentrates are not storage stable when admixed, that is, they are incompatible or reactive when combined and held over a prolonged period. Consequently, they cannot be pre-mixed, and sold and held in that form. The problem has arisen with the preparation of these mixtures in hospitals. Many alimentation solutions are used every day, and considerable time is spent in decanting and measuring the proper amounts of the various components and adding them to intravenous solutions. This procedure is also fraught with opportunities for error, mix-up and loss of sterility The present invention overcomes these problems by providing a completely closed system in which two, three, four or even more different components for alimentation can be packaged in proper concentration and ratios in a factory under rigid asceptic conditions, yet held in physical separation from each other to provide long-term storage stability and life, and yet are quickly and easily admixed at the time of use without opening of the system to the risk of contamination. The present invention significantly contributes to the saving of time and reduces the opportunities for mistakes and error in formulation. It is to be anticipated that this invention will be widely received and acclaimed by the health care profession.

SUMMARY OF THE INVENTION

Briefly, my invention comprises:

(1) a plurality of cylindrical rigid vials, each having a closed end and cylindrical walls, and containing a liquid concentrate of an alimentary component, a resilient piston stopper positioned approximately on the liquid surface within the vial and sealing same, (2) a transfer device for the sequential addition of the liquid contents of each of said vials to a conventional container of intravenous solution provided with an imperforate closure, said transfer device having a cannula, said cannula having a central portion which is provided with a longitudinally extending rigid support, in proximity to one end of said rigid support a laterally extending flange, one end portion of said cannula extending beyond said flange and being adapted to pierce the imperforate closure of said container of intravenous solution, said laterally extending flange being adapted to act as a stop to limit the extent of advancement of said cannula, the other end portion of said cannula extending beyond the other end of said rigid support and terminating in a sharpened outer end, a thin resilient tube over said sharpened outer end, said resilient tube being closed in proximity to the sharpened outer end and along the length of said other end portion of said cannula and having an open end which seals on said other end of said rigid support, said resilient tube being longitudinally compressible over and pierced by said sharpened outer end when the piston stopper of one of said vials is forced over said sharpened outer end whereby the contents of the vial can be transferred to the intravenous solution container through said cannula, said resilient tube being self-recoverable over said sharpened end when said piston stopper is withdrawn to maintain a seal over said cannula between the sequential additions of the liquid contents of each of said vials.

It is an object of this invention to provide a novel system for the containment of alimentary components.

It is a further object of this invention to provide a new and novel system of storing and using alimentary components.

It is still a further object of this invention to provide alimentary components for use in the health care professions whereby problems of incompatibility, loss of sterility and mix-ups are minimized.

These and other objects and advantages of my invention will be apparent from the detailed description which follows.

DESCRIPTION OF THE PREFERRED EMBODIMENTS

Figure 1:
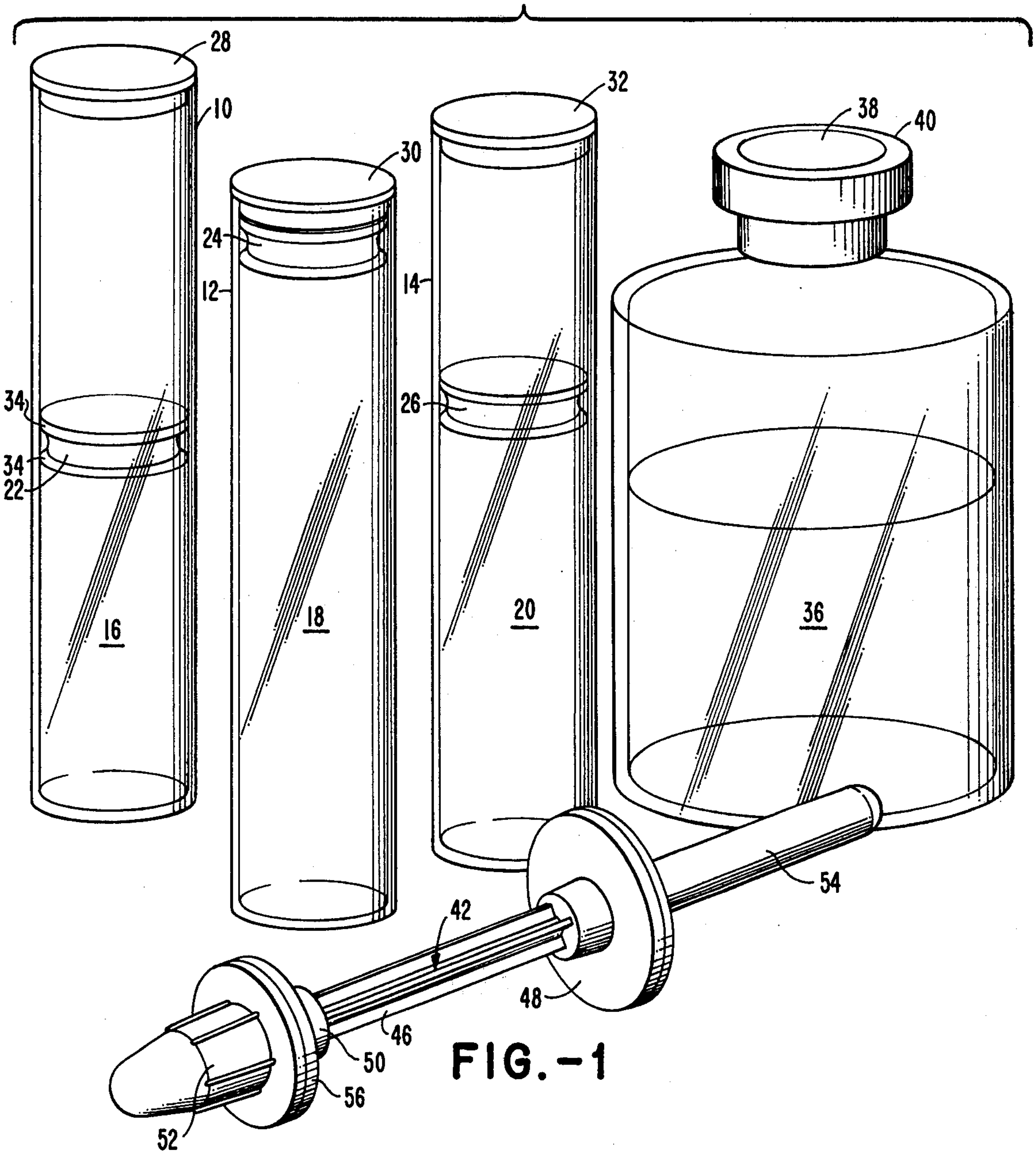
FIG. 1 is a perspective view of one embodiment of the novel alimentary kit of this invention, shown in conjunction with a typical bottle of intravenous solution.
Figure 2:
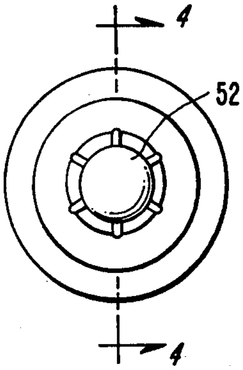
FIG. 2 is a left end view of the transfer device shown at the lower portion of FIG. 1.
Figure 3:
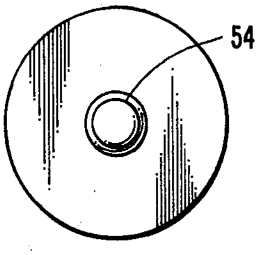
FIG. 3 is a right end view of the transfer device shown at the lower portion of FIG. 1.
Figure 5:
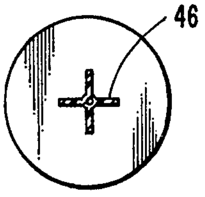
FIG. 5 is a sectional view taken along the line 5—5 in FIG. 4.
Figure 4:
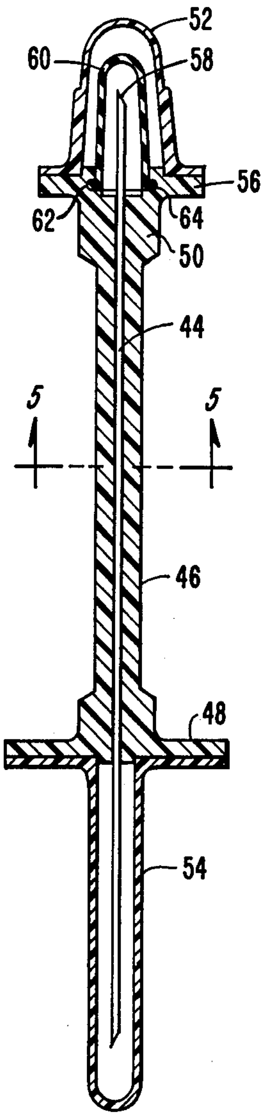
FIG. 4 is a sectional view taken along the line 4—4 in FIG. 2.

Turning to the drawings in greater detail, FIG. 1 shows three vials 10, 12 and 14 each containing a different liquid alimentary component 16, 18 and 20, respectively, which are sealed by piston stoppers 22, 24 and 26. Each vial also has an end or dust cap 28, 30 and 32 which are flicked away and discarded at the time of use. The piston stoppers 22, 24 and 26 are resilient, normally rubber compatible with the alimentary component, and may be provided with sealing rings 34.

The bottle of intravenous solution 36 is conventional, and is provided with a resilient closure 38 held by a peripheral crimped metal seal 40. The bottle can be replaced by a flaccid bag of intravenous solution, as will be apparent to those skilled in the art.

Figure 7:
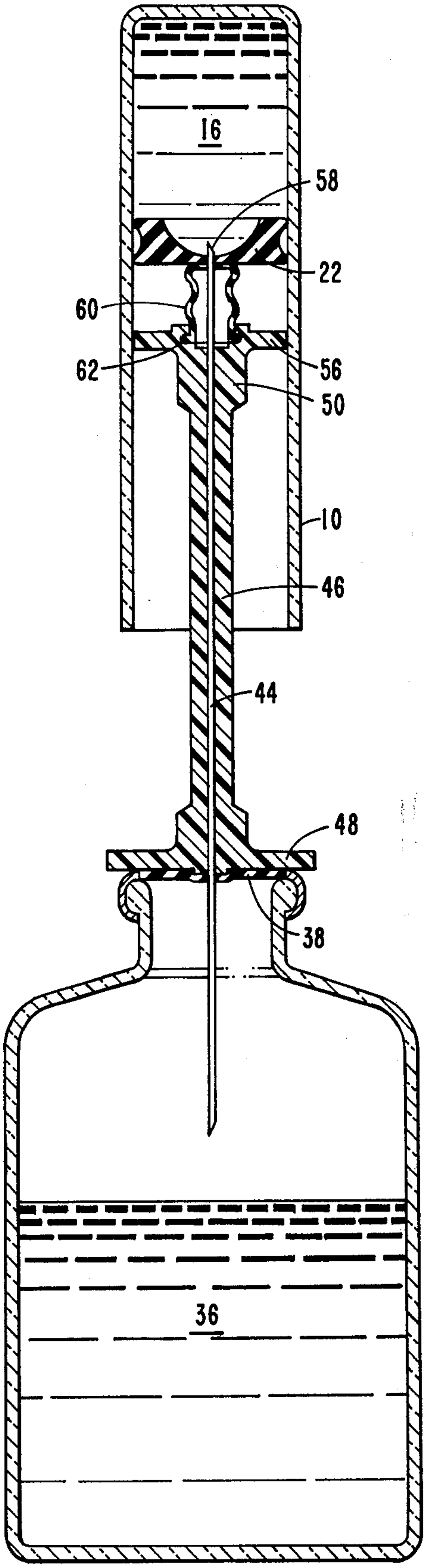
FIG. 7 shows the placement of one of the vials, containing an alimentary component in place and its contents about to be transferred to the intravenous solution bottle.
Figure 8:
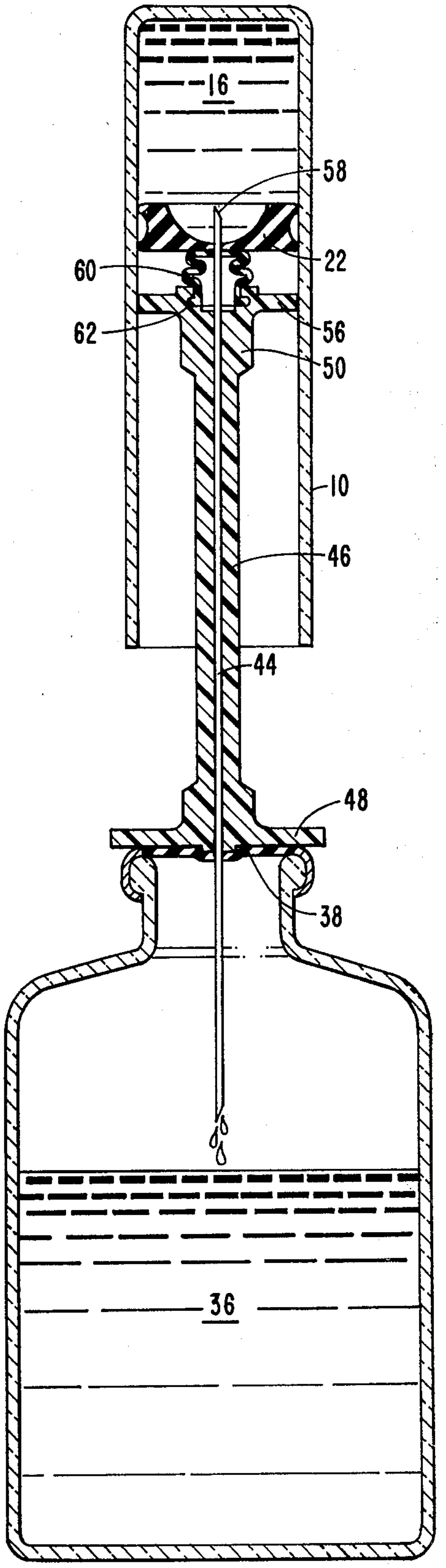
FIG. 8 shows in section the next phase of the transfer process, and follows in time the phase of FIG. 7.
Figure 9:
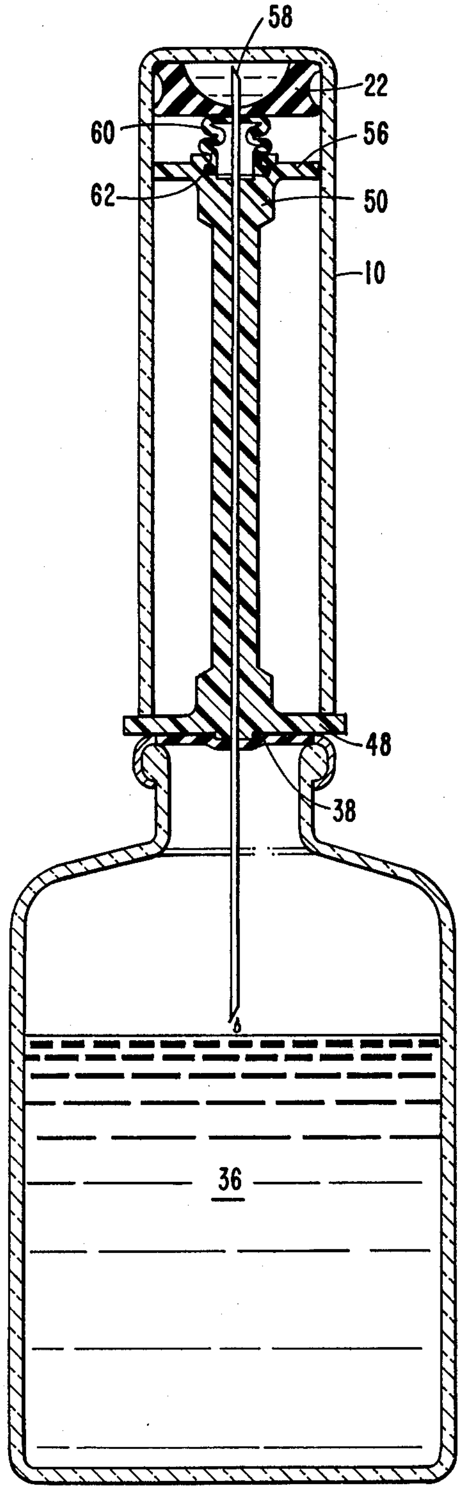
FIG. 9 shows in section the phase following FIG. 8.

The transfer device, generally 42, has a cannula 44, a longitudinally extending rigid support 46 surrounding the center portion of the cannula, one end of the support 46 terminates at flange 48 and the other end of support 46 terminating at the enlarged portion 50. Each end of the transfer device 42 is provided with a dust cover 52 and 54. The dust cover 52 seals on the flange 56 which has a smaller lateral dimension than the inside diameter of vials 10, 12 and 14, so that the latter may pass thereover, as shown in FIGS. 7–9.

Figure 10:
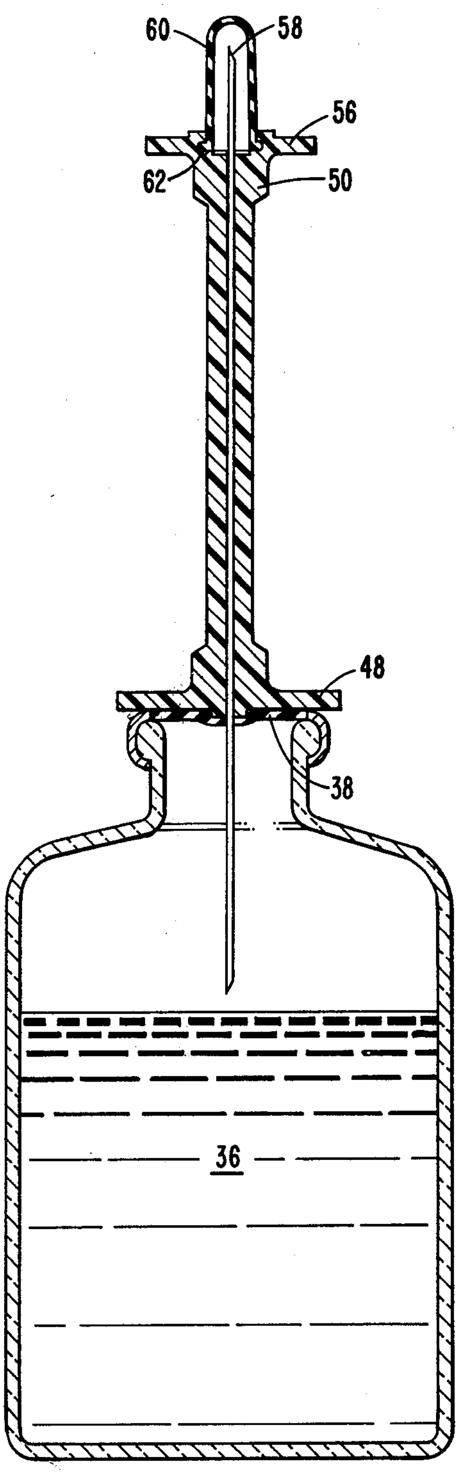
FIG. 10 shows the device after one vial of alimentary fluid has been transferred and awaiting the next vial.

The sharpened outer end 58 of cannula 44 is covered by resilient tube 60. The resilient tube 60 is pierced by sharpened outer end 58 when for example, the stopper 22 of vial 10 is forced over the end of the cannula 44 as shown in FIGS. 7 to 9. When the vial is removed, the resilient tube 60 snaps back over the sharpened outer end 58 to re-seal the transfer device, as shown in FIG. 10, until the next vial of alimentary component is brought into position for transfer to the intravenous solution bottle 36.

The resilient tube 60 forms a seal with recess 62 by virture of the integral external ring 64 on tube 60 which is received in recess 62. The resilient tube 60 is otherwise loosely positioned around the outside of the cannula and yet it is normally self sustaining in its lengthwise dimension until the vial stopper is applied to it.

Figure 6:
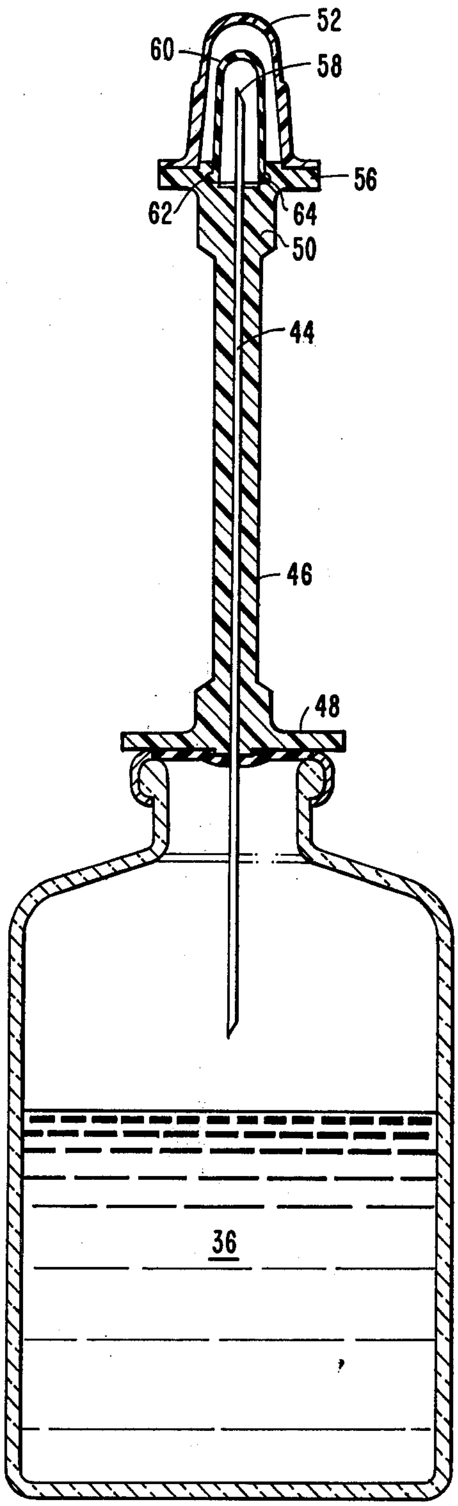
FIG. 6 is a sectional view showing the transfer device in place on a bottle of intravenous solution.

In operation, the cover 54 is removed and the transfer device 42 is positioned as shown in FIG. 6. The cap 52 is then discarded, and the system is ready to receive the fluid contents of the first vial in the kit. Once the contents of the first vial has been transferred, FIGS. 7 to 9, the system is ready for the next vial in the kit, and so on in sequence until all of the vial contents have been added to the intravenous solution bottle 36. Obviously, the kit of this invention may contain one, two, three, four or more separate vials.

Having fully described the invention, it is intended that it be limited only by the scope of the appended claims.

I claim:

1. An alimentation kit comprising:

(a) a plurality of cylindrical rigid vials, each having a closed end and cylindrical walls, and containing a liquid concentrate of an alimentary component, a slidable resilient piston stopper positioned approximately on the liquid surface within the vial and sealing same; and (b) a transfer device for the sequential addition of the liquid contents of each of said vials to a glass bottle containing intravenous solution and provided with an imperforate closure, said transfer device having a cannula, said cannula having a central portion which is provided with an elongated longitudinally extending rigid cannula support having a length approximately equal to the length of said vials, in proximity to one end of said rigid cannula support a first laterally extending flange, one end portion of said cannula extending beyond said first laterally extending flange and being adapted to pierce the imperforate closure of said bottle containing intravenous solution, said first laterally extending flange being adapted to act as a stop to limit the extent of advancement of said cannula and to abut said imperforate closure of said bottle containing intravenous solution, in proximity to the other end portion of said rigid cannula support a second laterally extending flange which is circular in shape and slightly smaller in diameter than the interior of said cylindrical walls of said rigid vials, the other end portion of said cannula extending beyond said second laterally extending flange and terminating in a sharpened outer end, a thin resilient tube over said sharpened outer end, said resilient tube being closed in proximity to the sharpened outer end and along the length of said other end portion of said cannula and having an open end provided with an external integral ring which is received in a complementary annular female groove in the walls of an axial cylindrical recess in said other end of said rigid support to form a seal therewith, said second laterally extending flange being slidably engageable with the interior of said cylindrical walls and said resilient tube being longitudinally compressible over and pierced by said sharpened outer end when one of said vials is fitted over said second laterally extending flange and the piston stopper of said one of said vials is forced over said sharpened outer end, said resilient tube being constructed and arranged to act in its compressed state as a stop for said piston stopper while said vial is advanced over said other end portion of said cannula and said other end of said rigid support, whereby said piston stopper can be slidably moved to the closed end of said vial and all of the contents of the vial can be transferred to the bottle of intravenous solution through said cannula, said resilient tube being self-recoverable over said sharpened end when said piston stopper is withdrawn to maintain a seal over said cannula between the sequential additions of the liquid contents of each of said vials.

* * * * *